United States Patent [19]

Stokes

[11] Patent Number: 4,552,979

[45] Date of Patent: Nov. 12, 1985

[54] PROCESS FOR TREATMENT OF UREA PLANT PROCESS CONDENSATE

[75] Inventor: Keith J. Stokes, Weston, Conn.

[73] Assignee: James Chemical Engineering Inc., Greenwich, Conn.

[21] Appl. No.: 644,355

[22] Filed: Aug. 27, 1984

[51] Int. Cl.$^4$ ............................................. C07C 126/06
[52] U.S. Cl. ........................................ 564/69; 564/73; 423/359
[58] Field of Search .................... 564/73, 69; 423/359

[56] References Cited

U.S. PATENT DOCUMENTS

| | | | |
|---|---|---|---|
| 3,292,998 | 12/1966 | James | 23/213 |
| 4,264,567 | 4/1981 | Pinto | 423/359 |
| 4,341,640 | 7/1982 | Landis | 564/73 |

OTHER PUBLICATIONS

James–Synthesis Gas Condensate Stripping–168th ACS National Meeting, Atlantic City, N.J., Sep. 11, 1974.

*Primary Examiner*—Charles F. Warren
*Assistant Examiner*—R. A. Picard
*Attorney, Agent, or Firm*—St. Onge Steward Johnston & Reens

[57] ABSTRACT

A process and apparatus are described which enable urea plant process condensate, which is contaminated with urea and other combined forms of ammonia and carbon dioxide, to be converted substantially completely and on a continuous basis, to a gaseous stream comprising steam, ammonia, carbon dioxide and hydrocarbon gas (introduced in the processing of the condensate). The gaseous stream so recovered is employed as feedstock for use in the reformer of the ammonia plant which supplies ammonia and carbon dioxide feedstocks for the synthetic urea plant from which the treated process condensate was derived. In a preferred embodiment the hydrocarbon fuel gas is natural gas. The process of the invention obviates the environmental and like problems hitherto encountered in the handling of urea plant process condensate and also provides marked advantages including improving the economics of operation of the urea plant and associated ammonia reformer plant.

16 Claims, 2 Drawing Figures

PROCESS FOR TREATMENT OF UREA PLANT PROCESS CONDENSATE

BACKGROUND OF THE INVENTION

1. Field of the Invention

This invention relates to a process and apparatus for the treatment of waste water containing nitrogenous materials and is more particularly concerned with a process and apparatus for the recovery of useful gaseous feedstocks from waste water contaminated with urea and like materials.

2. Description of the Prior Art

Urea is manufactured commercially by reacting ammonia with carbon dioxide. The reaction produces substantial amounts of water (one mole for each mole of urea produced). Illustratively, a 1900 short ton capacity urea plant produces about 50,000 pounds per hour of water in the urea reaction. An additional 20,000 pounds per hour of water is condensed from utility steam in those plants that have steam-motivated vacuum jets and this steam condensate is mixed with the water generated in the reaction. Urea and carbamate are separated from the reaction products leaving waste water (hereafter "process condensate") contaminated with minor amounts of urea and other combined forms of ammonia and carbon dioxide including ammonium carbonate, ammonium carbamate and the like (hereinafter referred to collectively as "urea values"). This process condensate must be treated to reduce the level of urea values before it can be utilized or discarded. If the condensate is not so treated, but is disposed of by other means which results in its introduction into natural waterways, the urea values therein promote algae growth. In addition, ammonia produced by hydrolysis of the urea values can prove toxic to fish in the waterways.

Similarly, if the process condensate is to be re-utilized, a circumstance which is of particular importance where the urea plant complex is located in a geographical area where fresh water is not abundant, the urea values must be reduced to a level at which they no longer cause corrosion problems in processing equipment before the recovered process condensate can be employed as, for example, cooling water, boiler feed water and the like.

Accordingly, it has hitherto been common practice to subject the recovered process condensate to hydrolysis and use a countercurrent stream of steam in a stripping tower to convert the urea values to ammonia and carbon dioxide. The waste water so recovered still contains sufficient contaminates to require further treatment with anti-corrosion agents before re-use in steel processing equipment. A recently described improvement in the hydrolytic treatment process (U.S. Pat. No. 4,341,640) requires the use of a vessel which contains a special liquid holding zone located within the vessel and substantially separated from the vapor streams passing through the vessels.

U.S. Pat. No. 4,264,567 at Col. 5, lines 1-16, makes brief mention of the use of urea process condensate to cool steam employed in a process for producing hydrogen feedstock.

In all the hydrolytic processes previously employed the main object has been to reduce or eliminate, as far as possible, the contaminants in the process condensate so as to render the water useful in the liquid state for other purposes such as cooling water, boiler feed water and the like and to reduce toxicity of the effluent water.

James U.S. Pat. No. 3,292,998 describes a process and apparatus for saturating a feed gas stream of carbon monoxide with water vapour prior to catalytic reaction to produce hydrogen and carbon dioxide. Pinto U.S. Pat. No. 4,072,625 describes a process and apparatus for saturating a hydrocarbon feedstock with water vapor prior to catalytic reforming. The hydrocarbon feedstock is brought into contact under pressure with water which has been heated by scrubbing the synthesis gas stream from the catalytic reaction. A very closely related process is discussed by G. R. James in a paper entitled Synthesis Gas Condensate Stripping presented at the 168th ACS National Meeting, Atlantic City, N.J. on Sept. 11, 1974.

I have now found that urea plant process condensate can be treated on a continuous basis and in a highly economical and efficient manner to convert substantially the whole of the process condensate to a gaseous stream which is especially adapted for use as feedstock for an ammonia plant reformer. The latter forms part of the plant complex utilized in the manufacture of urea.

The advantages in process economics, re-utilization of waste products, reduction in energy requirements and other benefits to be discussed below, which flow from my discovery will be readily apparent to one skilled in the art.

SUMMARY OF THE INVENTION

The invention comprises a continuous process for treatment of urea plant process condensate which process completely hydrolyzes the urea values originally present therein, utilizing both steam and hydrocarbon fuel gas as stripping agents, converts substantially all the water present in the process condensate to steam and generates, as the end product of the process, a gaseous stream comprising steam, hydrocarbon fuel gas, ammonia and carbon dioxide which stream can be utilized as feedstock for an ammonia plant reformer in which a gas rich in hydrogen and carbon monoxide is generated by catalytic steam reforming of the hydrocarbon fuel gas. Since the ammonia plant reformer generally forms an integral part of a plant complex for the synthesis of urea it will be seen that the process of this invention serves to complete a continuous processing cycle in which waste product from the urea synthesis is recycled as feedstock for the initial stage of said synthesis.

It is an object of the invention to reduce or eliminate the environmental problems hitherto encountered in the disposal of waste water streams from urea synthesis plants.

Another object of the invention is to convert the said waste water streams into useful gaseous feedstock which can be re-utilized in the synthesis of urea in a continuous cycle of operations.

It is a further object of the invention to reduce the overall capital costs in combined urea/ammonia plants by eliminating hydrolyzers conventionally installed as equipment in the urea synthesis plant, reducing the boiler capacity required for steam production, reducing consumption of boiler feedwater treatment chemicals, replacing stainless steel in certain processing areas by less costly carbon steel equipment, and the like.

It is still another object of the invention to drastically reduce the use of water in the ammonia-urea plant complex since the amount of water recovered from the urea plant process condensate in accordance with the process of the invention meets in large part the requirements of the ammonia plant's reforming and shift reactions.

A further object of the invention is to reduce the overall energy requirements in a combined urea/ammonia plant.

The foregoing and other objects and advantages of the invention will be apparent from the following description of certain preferred embodiments of the invention.

DETAILED DESCRIPTION OF THE INVENTION

Figure 1:
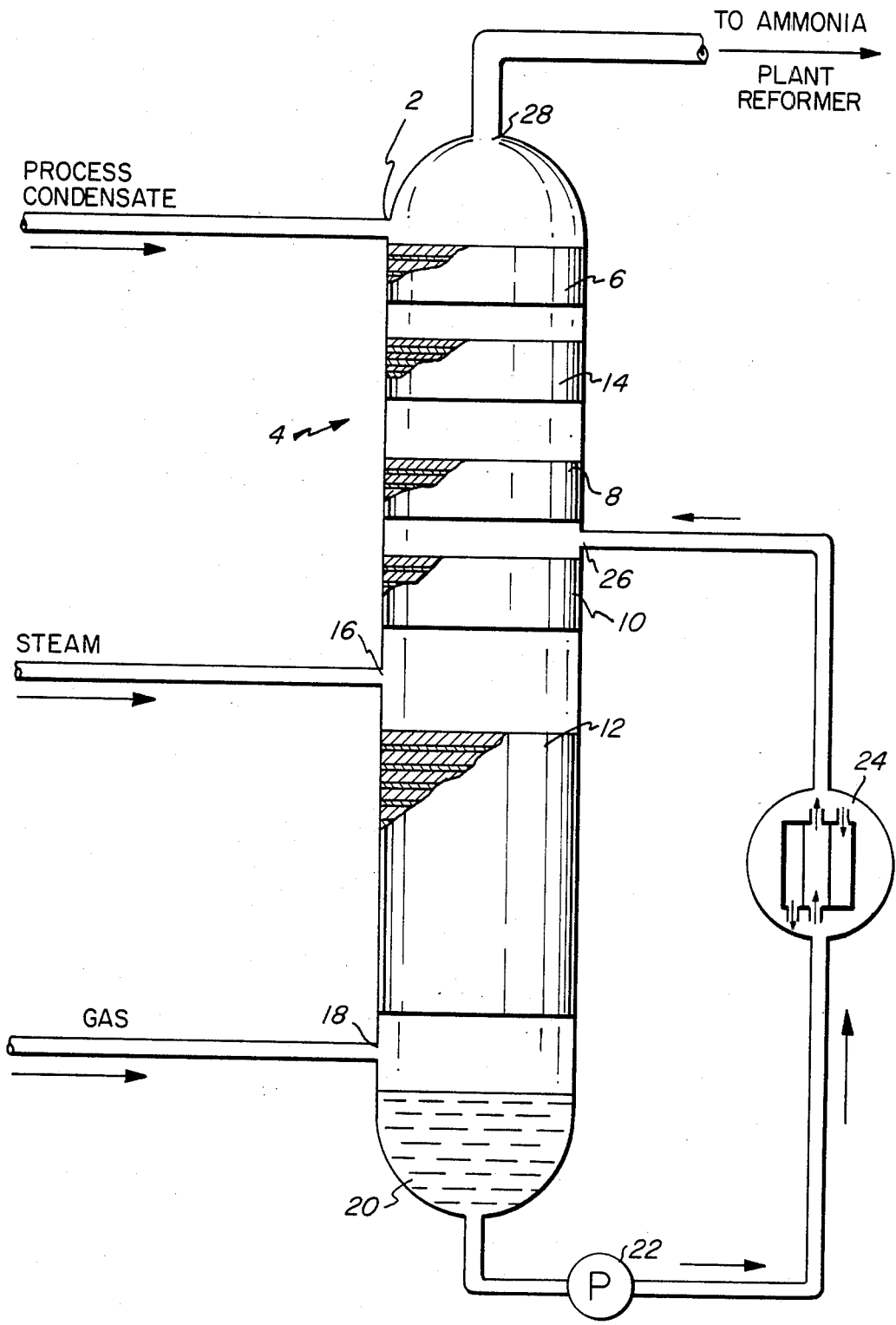
FIG. 1 is a schematic representation of a system in accordance with the invention.

Referring now to FIG. 1, urea plant process condensate is fed at (2) to stripper tower (4) which is provided with a series of stripping zones (6) (8) (10) and (12) which can be of any conventional construction. Illustratively, said zones are packed sections utilizing any conventional packing material supported by perforated trays. Interposed between stripping zones (6) and (8) is a hold-up or residence zone (14) which is constructed so as to require a predetermined period of time for the liquid process condensate, flowing downwardly under gravity, to pass completely therethrough. The residence zone (14) can take any of the forms conventional in the art for such zones. Illustratively the zone comprises a series of plates and overflow channels. The particular residence time required in this zone varies in accordance with a number of factors discussed more fully below.

Process steam is fed under pressure to the stripper tower (4) at (16) and hydrocarbon fuel gas is fed at (18). Liquid process condensate which collects at the base (20) of the stripper tower (4) is recycled via feed pump (22) and heat exchanger (24) and re-introduced into the stripper tower (4) at (26) located above stripping zone (10). Gaseous material is recovered overhead from exit port (28) and transferred as feedstock to an ammonia plant reformer (not shown).

The pressure employed in stripper tower (4) in any given instance is governed by the pressure employed in the downstream ammonia plant reformer to which the overhead from the stripper is being fed. Advantageously the pressure employed in stripper tower (4) is at about 20 psig greater than that being employed in the ammonia plant reformer. In most modern plants the reformer pressure is of the order of 500 to 580 psig and, accordingly, the pressure in the stripper tower (4), when employed in conjunction with such plants, is in the range of 520 to 600 psig. In older reformer designs the operating pressure is lower than 500 psig and the pressure employed in the striper tower (4), when used in conjunction with such plants, is correspondingly lower but still at about 20 psig higher than the pressure in the reformer.

Process condensate leaving a urea plant which has a hydrolyser based treatment section can have urea values as low as about 0.001 to 0.01 percent w/w. Process condensate from plants which have no such treatment section have much higher urea values and such values can reach as high as about 7.5 percent w/w. As will be apparent to one skilled in the art, the precise operating conditions and the dimensions of the various stripping zones in the stripper tower (4) will vary depending on the level of urea values in the process condensate which is to be subjected to treatment. The particular conditions which are described below are applicable to the treatment of process condensate containing urea values in the high end of the above range i.e. process condensate derived from urea plants which have no treatment section designed to reduce the urea value. As previously pointed out, the ability of the process and apparatus of the invention to handle process condensate from such plants is a significant advance in the art.

Using an operating pressure of the order of 600 psig in the stripper tower (4) the process condensate is fed continuously to the stripper (4) at entry port (2) after being preheated to a temperature advantageously of the order of 380° to 500° F. and preferably of the order of 400° to 450° F. The temperature of the process condensate remains within these ranges during passage downwardly through the various stripping zones. Some stripping of ammonia and carbon dioxide and hydrolysis of urea values occurs in the first stripping zone (6) and the hydrolysis of the urea values is substantially completed in the residence zone (14). The residence time of the condensate in this zone is adjusted so that approximately 99 percent of the urea values originally present in the process condensate have been hydrolized to ammonia and carbon dioxide by the time the liquid process condensate leaves the zone and passes downwardly to the next stripping zone (8). The residence time necessary to achieve this result varies depending on a number of factors including the temperature prevailing in zone (14) and the level of urea values in the process condensate being treated. In general the residence time lies within the range of about 2 to 10 minutes. The optimum residence time to be employed in any particular instance can be readily determined by a process of trial and error.

The bulk of the ammonia and carbon dioxide present in the process condensate as it flows downwardly into stripping zone (8) is stripped therefrom in said zone by vapor (steam and hydrocarbon gas) rising countercurrently through the zone. The process condensate leaving zone (8) is combined with recirculated condensate entering at (26). The latter condensate has been pumped from the base (20) of the stripper tower (4) via heat exchanger (24) which raises the temperature of the condensate to a temperature of the order of 380° F. to about 460° F. Advantageously the temperature of the condensate being recirculated is raised to the temperature of the vapor stream passing upwardly through the stripper zone (10) so that no appreciable condensation of steam occurs in this zone. In the example being discussed the temperature of the vapor stream is of the order of about 455° F.

Figure 2:
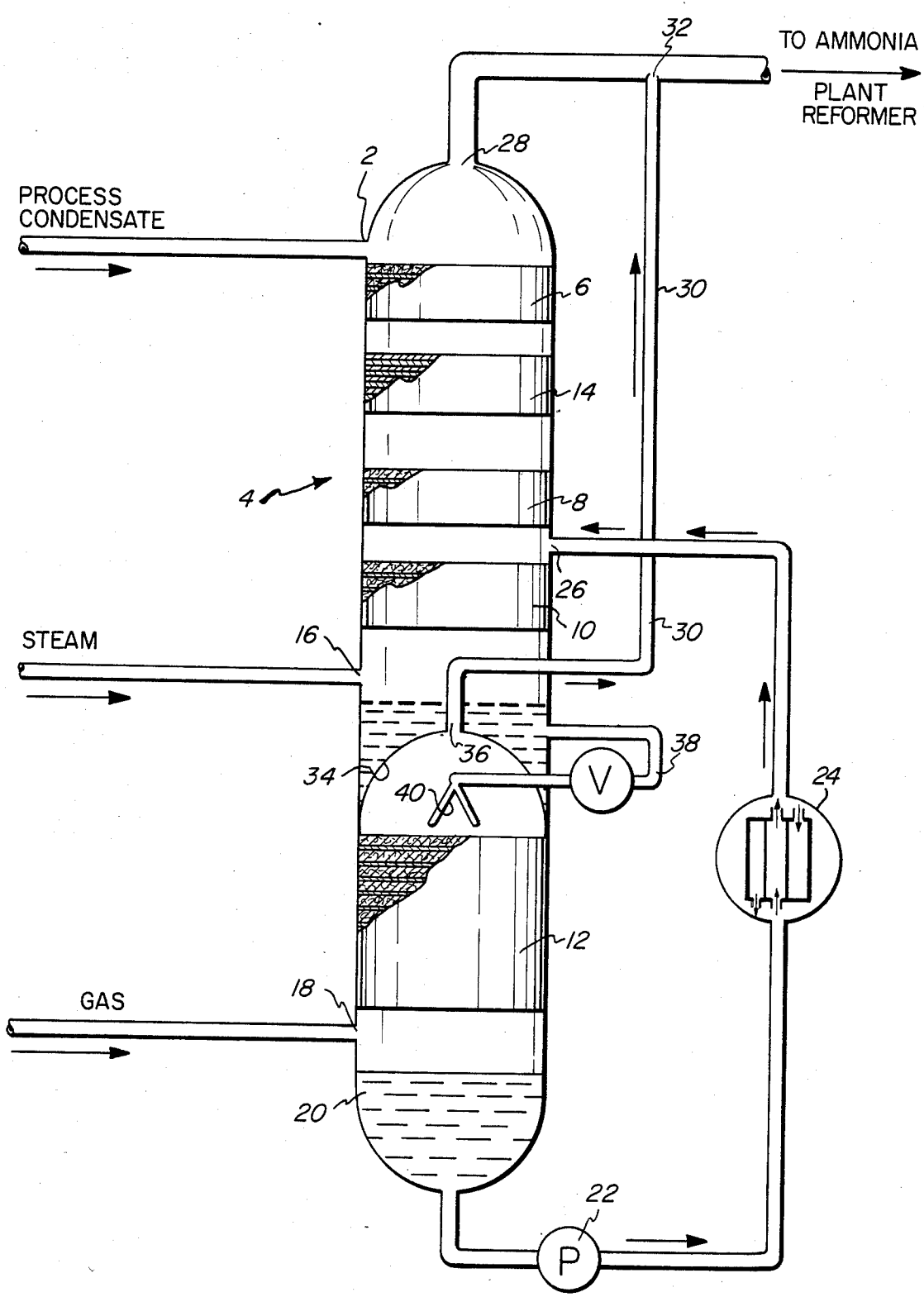
FIG. 2 is a schematic representation of a modification of the system shown in FIG. 1.

The mixed stream of process condensate flowing downwardly from stripping zone (8) and recirculated process condensate entering at (26) is subjected to steam stripping in zone (10) using the steam entering at (16) as shown in both FIGS. 1 and 2. This process steam contains no ammonia or carbon dioxide and can be saturated or superheated.

The process condensate flowing downwardly from stripping zone (10) to stripping zone (12) generally contains of the order of 0.1 to about 0.5 percent urea values in the particular example being discussed. Hydrocarbon gas is introduced at (18) below the stripping zone (12).

This gas can be at ambient temperature or can be preheated to a temperature up to about 450° F. depending upon the amount of heat which it is desired to introduce into the system at this point. The passage of the gas upwardly through the stripper tower (4) serves to strip out ammonia and carbon dioxide. However, where the hydrocarbon gas introduced at (18) itself contains carbon dioxide gas at a level such that the partial pressure of carbon dioxide in the hydrocarbon exceeds that of the carbon dioxide generated in the stripper tower (4) it is necessary to use a modified form of stripper (4) as discussed below.

In the stripping zone (12) water in the downwardly flowing stream of process condensate and recirculated condensate is converted to steam at such a rate that the overall system has no liquid effluent except for a very small blowdown, of the order of about 0.5 to 1.5 percent by weight of initial feed, which may be necessary in certain instances to remove non-volatile contaminants such as chloride ions.

As will be apparent to one skilled in the art, the dimensions of the various stripping zones required in any given instance will depend largely on the urea values present in the condensate and the partial pressures of ammonia and carbon dioxide generated therefrom. The data reported by Van Krevelen et al., Rec. trav. chim. 68, 193, 1949 for the vapor pressure of ammonia and carbon dioxide over such condensate solutions serves as a guide in determining appropriate dimensions of the stripping zones.

The stream of hydrocarbon gas which is introduced at (18), the stream of process steam introduced at (16) and the steam which has been generated by vaporization of water in the process condensate all pass upwardly in the stripper column (4) and scrub out the ammonia and carbon dioxide which has been liberated by hydrolysis of the urea values in the process condensate. A gaseous stream comprising steam, hydrocarbon gas and entrained ammonia and carbon dioxide is removed overhead at (28) and conducted as feedstock to an ammonia plant reformer. The latter normally requires a feedstock having a ratio of proportions by volume of steam to hydrocarbon fuel gas within the range of about 2.6:1 to 4:1. As will be obvious to one skilled in the art, the proportions of these two components in the gaseous overhead produced in accordance with the invention can be readily controlled within the above range by appropriate adjustment of rates of feeding of hydrocarbon fuel gas and process steam and the rate of production of steam in situ in the stripper column (4).

The term "hydrocarbon gas" as employed herein is inclusive of natural gas and volatile hydrocarbons such as refinery off gases and the like. Natural gas is a preferred hydrocarbon gas for use in the process of the invention.

It will be observed that the only external source of heat used to raise the temperature of the process condensate takes the form of a heat exchanger (24). The condensate does not pass through a conventional boiler in the course of the process of the invention. The use of anti-corrosion chemicals required in boiler feed water is thus avoided. Further, the use of increased boiler capacity for steam production is avoided. Indeed, it is possible to reduce boiler capacity for the urea/ammonia complex because the process of the invention provides the steam for the feed to the ammonia plant reformer which steam was previously generated by boiler.

Further, the recycle stream of process condensate which is being pumped around the loop from the base (20) of the stripper tower (4) via pump (22) and heat exchanger (24) to entry point (26), has already been subjected to hydrolysis of the urea values in a series of strippers and in the residence or holdup zone (14) before reaching the recycle loop. Accordingly, the level of contaminants in the fluid being circulated around the recycle loop is so low that, in many cases, it presents little or no corrosion problem unlike the process condensate which is being treated in the upper stages of the stripper (4). In such cases the stainless steel equipment, which it is essential to use in conventional handling of such process condensates, can be dispensed with in that section of the stripper (4) which forms part of the recycle section, i.e., that part of the stripper (4) which lies at or below the point of entry (26) of the recycle stream and this particular section can be fabricated from carbon steel rather than stainless steel. This factor alone represents a very substantial savings in capital cost of the eqipment.

In FIG. 2 there is drawn a modification of the system illustrated in FIG. 1. This modification is employed when the hydrocarbon fuel gas feed employed in the process of the invention has a content of carbon dioxide at a level such that the partial pressure of the latter in the fuel gas feed would exceed the partial pressure of carbon dioxide generated by hydrolysis in the stripper (4). The elements in FIG. 2 which correspond to those in FIG. 1 are identified by the same numbering. The modification introduced in FIG. 2 comprises means to collect gaseous overhead from the stripper zone (12) and convey this overhead via duct (30) to be combined at (32) with the gaseous overhead taken from the exit port (28). This is achieved by introducing a cap (34) fitted with exit port (36) above the stripping zone (12) and also providing a liquid bypass (38) to conduct liquid collecting above cap (34) to a liquid distributing device (40) which serves to deliver the liquid to the top of stripping zone (12).

The process of the invention is conducted in the same manner and under substantially the same operating parameters discussed above when using the device shown in FIG. 2.

It is to be understood that the specific best mode embodiments of the invention described above have been given for purposes of illustration only and are not to be construed as limiting.

The process and apparatus of this invention enable one to achieve a marked improvement in the overall economics of operation of a urea plant complex. Not only does the process completely eliminate all environmental concerns associated with the previous need to dispose of process condensate, but it enables substantially the whole of the process condensate generated by the urea plant to be converted into feedstock which can be recycled to the ammonia plant reformer associated with the urea plant. Further the need for large quantities of feed water for the complex is substantially reduced because water required (in the form of steam) for the ammonia plant reformer is generated in accordance with the process of the invention by recycling of the process condensate. This is of particular importance when the urea plant complex is located in areas where fresh water is not abundant.

A particularly valuable application of the process and apparatus of the invention lies in the use thereof in urea plant complexes which are located offshore on marine platforms or barges in order, for example, to utilise the natural gas from offshore wells. In such locations the only source of water is usually that from the ocean and this water as to be desalinated before utilisation. Accordingly the low water requirements of a urea plant complex which incorporates the process and apparatus of this invention represent a highly significant advantage in such situations.

What is claimed is:

1. In a continuous process for the treatment of process condensate from a synthetic urea plant, said condensate containing urea values, the steps comprising:
    (a) continuously subjecting said concentrate to the action of steam introduced countercurrently in a series of stripping zones, the residence time in at least one of said zones being sufficient to effect hydrolysis of a major portion of said urea values to yield ammonia and carbon dioxide;
    (b) continuously subjecting the partially stripped process condensate to further stripping using a stream of hydrocarbon gas introduced counter-currently under pressure;
    (c) continuously collecting liquid condensate from the latter step, passing the same through a heat exchanger to raise the temperature thereof and recycling the heated liquid to one of the first series of stripping zones; and
    (d) continuously recovering as overhead from the first of the stripping zones, a gaseous stream comprising steam, hydrocarbon gas, ammonia and carbon dioxide; wherein substantially the whole of the process condensate introduced in step (a) is continuously converted into steam, ammonia and carbon dioxide and recovered in said gaseous stream taken as overhead.

2. The process of claim 1 wherein the aqueous process condensate is preheated to a temperature in the range of about 380° F. to 500° F. prior to passage through the initial series of stripping zones in step (a).

3. The process of claim 1 wherein the residence time in at least one of said series of stripping zones in step (a) is of the order of about 2 minutes to about 10 minutes.

4. The process of claim 1 wherein the condensate collected in step (c) is heated to a temperature of the order of 380° F. to 460° F. before being recycled to the first series of stripping zones.

5. The process of claim 1 wherein the hydrocarbon gas is natural gas.

6. The process of claim 1 wherein the gaseous stream recovered overhead in step (d) is recycled as feedstock to the reformer of the ammonia plant employed to generate ammonia feedstock for said synthetic urea plant.

7. The process of claim 1 wherein the gaseous stream recovered overhead from the further stripping step (b) is separately collected and combined with the gaseous stream recovered in step (d).

8. In a continuous process for the treatment of aqueous process condensate from a synthetic urea plant said condensate containing urea values as contaminants the steps comprising:
    (a) continuously subjecting said condensate to the action of steam under pressure while causing said condensate to flow sequentially through (i) at least one stripping zone, (ii) a zone in which the residence time is sufficient to effect hydrolysis of the major portion of the urea values originally present in the process condensate, and (iii) at least two additional stripping zones;
    (b) continuously subjecting the partially stripped process condensate to the action of a stream of natural gas under pressure in a further stripping zone;
    (c) continuously recovering liquid process condensate from step (b) and recycling the same at elevated temperature to one of the additional stripping zones (iii) employed in step (a); and
    (d) continuously recovering as overhead from the first stripping zone employed in step (a) a gaseous stream comprising steam, natural gas, ammonia and carbon dioxide;
wherein substantially the whole of the process condensate introduced in step (a) is continuously converted into steam, ammonia and carbon dioxide and recovered in said gaseous stream taken as overhead.

9. The process of claim 8 wherein the aqueous process condensate is preheated to a temperature in the range of about 400° F. to about 450° F. during its passage through the various zones in step (a).

10. The process of claim 8 wherein the residence time in zone (ii) in step (a) is of the order of about 2 minutes to about 10 minutes.

11. The process of claim 8 wherein the liquid process condensate recovered in step (c) is heated to a temperature of the order of 380° F. to 460° F. by passage through a heat exchanger prior to introduction to the additional stripping zone (iii).

12. The process of claim 8 wherein the proportion of natural gas introduced in step (b) to total steam including that introduced in step (a) and that generated in situ by vaporization of process condensate water is such that the ratio of steam to natural gas in the gaseous stream recovered overhead in step (d) is in the range of 2.6:1 to 4:1 by volume.

13. The process of claim 12 wherein the gaeous stream recovered overhead is recycled as feedstock to the reformer of the ammonia plant employed to generate ammonia feedstock for said synthetic urea plant.

14. The process of claim 8 wherein the gaseous stream recovered overhead from step (b) is collected separately and combined with the gaseous stream recovered overhead from the first of the stripping zones.

15. In a process for the preparation of feedstock for an ammonia plant reformer the steps comprising:
    (a) subjecting urea plant process condensate containing urea values to the action of steam under pressure in a series of stripping zones to hydrolyze the major portion of said urea values to ammonia and carbon dioxide;
    (b) subjecting the partially stripped condensate to further stripping using a stream of natural gas;
    (c) collecting liquid process condensate from step (b) and recycling the same at elevated temperature to one of the first series of stripping zones; and
    (d) collecting the gaseous comprising steam, natural gas, ammonia and carbon dioxide, from the first of the stripping zones;
wherein substantially the whole of the urea plant process condensate introduced in step (a) is converted into steam, ammonia and carbon dioxide and recovered in said gaseous stream taken as overhead for use as ammonia plant reformer feedstock.

16. The process of claim 15 wherein the gaseous stream recovered overhead from step (b) is collected separately and combined with the gaseous stream recovered overhead from the first of the stripping zones.

* * * * *